(12) United States Patent
Tozzi

(10) Patent No.: US 9,101,538 B2
(45) Date of Patent: Aug. 11, 2015

(54) INJECTABLE AMINO-ACID COMPOSITION

(71) Applicant: Donna M. Tozzi, Montvale, NJ (US)

(72) Inventor: Donna M. Tozzi, Montvale, NJ (US)

(*) Notice: Subject to any disclaimer, the term of this patent is extended or adjusted under 35 U.S.C. 154(b) by 0 days.

(21) Appl. No.: 13/854,955

(22) Filed: Apr. 1, 2013

(65) Prior Publication Data

US 2013/0287758 A1    Oct. 31, 2013

Related U.S. Application Data

(63) Continuation-in-part of application No. 12/784,245, filed on May 20, 2010, now abandoned.

(60) Provisional application No. 61/179,980, filed on May 20, 2009.

(51) Int. Cl.

| | | |
|---|---|---|
| A61K 31/74 | (2006.01) |
| A61Q 5/02 | (2006.01) |
| A61Q 5/12 | (2006.01) |
| A61K 45/00 | (2006.01) |
| A61K 47/00 | (2006.01) |
| A61K 9/00 | (2006.01) |
| A61K 31/401 | (2006.01) |
| A61K 38/48 | (2006.01) |
| A61K 31/198 | (2006.01) |
| A61K 31/7008 | (2006.01) |
| A61K 31/4415 | (2006.01) |
| A61K 31/4172 | (2006.01) |
| A61K 8/44 | (2006.01) |
| A61K 8/49 | (2006.01) |
| A61K 8/64 | (2006.01) |
| A61Q 19/08 | (2006.01) |
| A61Q 19/00 | (2006.01) |

(52) U.S. Cl.
CPC ............. *A61K 9/0019* (2013.01); *A61K 8/44* (2013.01); *A61K 8/4946* (2013.01); *A61K 8/64* (2013.01); *A61K 31/198* (2013.01); *A61K 31/401* (2013.01); *A61K 31/4172* (2013.01); *A61K 31/4415* (2013.01); *A61K 31/7008* (2013.01); *A61K 38/4893* (2013.01); *A61Q 19/00* (2013.01); *A61Q 19/08* (2013.01); *A61K 2800/91* (2013.01)

(58) Field of Classification Search
CPC ........ A61Q 19/00; A61Q 19/08; A61K 38/00
See application file for complete search history.

(56) References Cited

U.S. PATENT DOCUMENTS

| | | |
|---|---|---|
| 4,308,257 A | 12/1981 | Caspe |
| 5,256,140 A | 10/1993 | Fallick |
| 5,869,068 A | 2/1999 | De Lacharriere et al. |
| 5,976,559 A | 11/1999 | De Lacharriere et al. |
| 6,284,284 B1 | 9/2001 | Naughton |
| 6,660,301 B1 | 12/2003 | Vogel et al. |
| 7,015,198 B1 | 3/2006 | Orentreich et al. |
| 7,192,984 B2 | 3/2007 | Berg et al. |
| 7,312,198 B2 | 12/2007 | Kiss |
| 7,491,709 B2 | 2/2009 | Carey |
| 2004/0259245 A1* | 12/2004 | Thorel et al. .............. 435/366 |
| 2007/0258935 A1* | 11/2007 | McEntire et al. .......... 424/70.11 |
| 2009/0068255 A1* | 3/2009 | Yu et al. .................... 424/450 |
| 2012/0135937 A1* | 5/2012 | Bertholon et al. .......... 514/18.8 |

OTHER PUBLICATIONS

Berbos et al., Curr Opin Opathalmol, 2010; 21: 387-395.*
Jordan, Carin Granstrom, carnosine; nature's Pluripotent Life Extension Agent, Life Extension, Jan. 2001.
Carnosine and Cellular Senescence, LifeExtension, Jan. 2001.
Tozzi Skincare (Dermatology Times, Apr. 1, 2008).

* cited by examiner

*Primary Examiner* — Gary Nickol
*Assistant Examiner* — Lakia Tongue
(74) *Attorney, Agent, or Firm* — Assouline & Berlowe; Loren Donald Pearson; Greg Popowitz

(57) ABSTRACT

An injectable amino-acid composition acts naturally to fuel collagen synthesis, which retards aging and helps to clear cellular decay while accelerating the cell division that promotes healthy, younger looking skin. The amino-acid composition includes carnosine. The composition is injected into the dermis of patients. The composition can be used in conjunction with botulinum toxin and fillers to enhance their effectiveness and extend their usefulness.

16 Claims, 6 Drawing Sheets

INJECTABLE AMINO-ACID COMPOSITION

CROSS-REFERENCE TO RELATED APPLICATIONS

This is a continuation-in-part application of application Ser. No. 12/784,245, filed May 20, 2010, which claims the benefit of U.S. Provisional Application No. 61/179,980, filed May 20, 2009. The contents of both applications are hereby incorporated by reference.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

FIELD OF THE INVENTION

The invention relates to injectable amino-acid compositions for dermatologic treatments.

2. Description of the Related Art

Aging, sun (i.e. ultraviolet (UV) light), smoking, and other conditions can damage, wrinkle, and discolor the skin. Treatments and products (including anti-aging creams) promise to reduce, remove, or prevent age-related wrinkles. Despite great demand, most such products and treatments have not been proven to give lasting or major positive effects. Stretching the skin via a surgical procedure called a "face lift" can remove some wrinkles.

Amino acids are building blocks for proteins. Essential amino acids cannot be made by the human body but are still needed. Accordingly, essential amino acids must introduced by other means.

Proteins are a component of all cells and are needed when the body replaces its own damaged tissue.

The dermis is a layer of skin between the epidermis and subcutaneous tissues, and is composed of two layers, the papillary and reticular dermis. Structural components of the dermis are collagen, elastic fibers, and extrafibrillar matrix (previously called ground substance).

Delivering amino acids to the dermis has been troublesome. Topical applications in the form of ointments do not penetrate the epidermis effectively to reach the dermis in sufficient quantities. Furthermore, topically administered amino-acid compositions are easily removed and wiped from the epidermis. Other known means of administering amino-acids are ineffective.

While topical treatments are ineffective, injectable wrinkle treatments are growing in popularity. Injections of botulinum toxin such as those sold under the trademark BOTOX® are used to paralyze muscles. Paralyzed muscles are unable to contract and form wrinkles. The injections need to be periodically repeated and are performed by a physician. As a result, there is a need to reduce the need for botulinum-toxin injections and to maximize the efficacy of the botulinum-toxin injections.

Injectable fillers such as those sold under the trademark RESTYLANE® are also growing in popularity. Injectable fillers fill in wrinkles in the skin. In addition, they can be used to augment tissue, like the lips. The injectable filler sold under the trademark RESTYLANE® uses hyaluronic acid as its main ingredient.

Usala (U.S. 2002/0065222, 2001/0019841, and 2001/0007658) teach a "Method of Stimulation Hair Growth." The documents include a method for stimulating hair growth that involves injecting a composition into an intradermal or subdermal site. The composition being injected includes (polar) amino acids. The composition includes a matrix of gelatin/long chain carbohydrates. Within the matrix are polar amino acids: arginine, lysine, histidine, glutamic acid, and aspartic acid. Usala teaches a method for stimulating hair growth but does not contemplate any improvements to surrounding skin tissue.

De Lacharriere et al. (U.S. Pat. Nos. 5,976,559 and 5,869,068) teach, "Compositions and Methods for Treating Wrinkles and/or Fine Lines of the Skin." The document involves a topical and an injectable composition. The composition includes at least one agonist substance of at least one receptor associated with at least one chlorine channel present in cutaneous tissue. Examples of agonists according to De Lacharriere are detailed on col. 4, lines 8-22.

Carey (U.S. Pat. No. 7,491,709) teaches a, "Treatment with Hyaluronic Acid." The method calls for large volume (i.e. an entire syringe) of Hyaluronic acid (HA) at targeted places. The injection is into the deep fat layer of the skin, just above the bone. The injection can be at a site to be filled, in particular, the upper middle face and check. Carey '709 does not teach injecting an amino-acid composition into the dermis of the skin.

Azar (US 2009/0275917) teaches a, "Skin Treatment System and Method." The device provides multi-site intra-dermal injection of medication.

Vogel et al. (U.S. Pat. No. 6,660,301) teaches, "Injectable Microspheres for Dermal Augmentation and Tissue Building." The microspheres are polymers coated with a positively charged cell adhesion promoters and autologous cells. Vogel et al. is a filler and does not involve amino acid compositions.

Orentreich et al. (U.S. Pat. No. 7,015,198) teaches, "Materials for Soft Tissue Augmentation and Methods of Making and Using Same." Orentreich et al. teaches an injectable filler made from cross-linked blood plasma proteins.

Caspe (U.S. Pat. No. 4,308,257) teaches an, "Accelerating Cellular Repair Composition for the Human Body and Method of Administering Same." Caspe teaches a two step method. The first method includes a subcutaneous injection of a pyrogen-free liquid including arginine, thiamine sale, conenzyme-1, and diaphorase flavin protein enzyme. The second treatment involves ingestion of tablets including nicotineamide, adenosine-5-monophoasphate, codehydrogenase (coenzyme-1), and inert carrier. The injections are subcutaneous and not into the dermis. The injections are not delivered to the site to be treated.

Naughton (U.S. Pat. No. 6,284,284) teaches, "Compositions and Method for Production and Use of an Injectable Naturally Secreted Extracellular Matrix." The Extracellular matrix is an injectable filler based on an extracellular matrix covered with stromal cells. The composition does not involve amino acids.

Accordingly, there exists a need to provide a formulation of amino-acid that can be delivered directly to the dermis of a patient.

In addition there exists a need for a composition and treatment that increases the effectiveness and duration of other injectable treatments.

BRIEF SUMMARY OF THE INVENTION

It is accordingly an object of the invention to provide a method for promoting skin repair by delivering an amino acid composition to a dermis of a patient and amino-acid composition that overcome the above-mentioned disadvantages of the heretofore-known methods and compositions of this general type.

With the foregoing and other objects in view there is provided, in accordance with the invention, a method and a composition for promoting tissue repair in the skin of a patient. The method involves delivering an amino-acid composition to a dermis layer of skin of a patient. Typical locations to be treated include the face of the patient. More particularly, locations to be treated include the skin surrounding the eyes, the cheeks, the upper lip, the oral commissures, and the jaw line. Other areas that can be treated include the neck, décolleté, cleavage, and hands of a patient.

When delivered to the dermis, the amino-acid composition acts naturally to fuel collagen synthesis. Collagen synthesis retards aging and helps to clear cellular decay while accelerating the cell division that promotes healthy, younger-looking skin. The amino-acid composition promotes repair of the skin's structure at a cellular level. The amino-acid composition helps to increase the production of collagen in the dermis. As a result of the composition on the cells in the dermal layer, the skin is suppler, firmer, smoother, and fine lines and wrinkles are softened. The composition works to create healthy skin. Treatments with the composition have a cumulative effect.

The composition is injected alone or before dermal fillers or botulinum toxin injections, such as those sold under the trademark BOTOX®. Delivering the amino-acid composition to the dermis where a subsequent treatment is to be injected creates a healthy environment for revitalization. Bruising and inflammation are typical complications following any injection, in particular, a filler injection. Injecting a site with the amino-acid composition before subsequent injections quickens healing times following botulinum toxin injections, such as those sold under the trademark BOTOX®, and filler injections.

The amino-acid composition can be delivered to the dermis by injection. A preferred volume of solution is one tenth of a milliliter (0.1 mL). The amino-acid composition can be delivered on the same day as other injections, such as botulinum toxin and fillers. In a preferred method, the amino-acid composition is first injected into the dermis, next botulinum toxin or a filler is injected. If botulinum toxin and a filler are both to be injected, the preferred order of injection is amino-acid composition, then filler, then botulinum toxin. To aid in healing, the amino-acid composition is injected one week following other injections of botulinum toxin or a filler.

A syringe can be used to inject the amino-acid composition into the dermis. The distal tip of the hollow needle is inserted into the dermis. Then, the amino-acid composition is delivered to the dermis via the hollow needle.

The composition can be used alone or prior to dermal filler and botulinum-toxin injections. The composition is not a neurotoxin or a filler.

The composition enhances the results of fillers and botulinum-toxin injections. In addition, the composition prolongs the effects of fillers and botulinum-toxin injections.

The composition can improve results from subsequent filler and botulinum-toxin injections in patients who have previously received dermal fillers. The composition strengthens the dermis prior to the injecting of fillers and botulinum-toxin. As a result, the composition creates longer-lasting and better results.

The composition when injected produces a fresh, toned, revitalized appearance.

The composition includes amino acids that rejuvenate the skin when injected into the dermis layer. The composition includes at least two of the following amino acids: arginine, isoleucine, leucine, lysine, methionine, and proline. The amino acids of the composition have been found to produce better effects when used together than separately.

The composition can include additional ingredients that are beneficial for the skin. The extracts include B vitamins, DMAE (dimethylaminoethenol) and glucosamine for healthy tissue structure, increased hydration, clarity, and de-pigmentation.

Arginine increases secretion of insulin, glucagon, and growth hormones. In addition, Arginine aids in the formation of collagen, healing, and immune system stimulation. Arginine (abbreviated as Arg or R) is an $\alpha$-amino acid. The L-form is one of the twenty most common natural amino acids. FIG. 1 shows the chemical formula for Arginine.

Isoleucine is used for energy by muscle tissue and helps prevent muscle wasting. Isoleucine (abbreviated as Ile or I) is an $\alpha$-amino acid with the chemical formula $HO_2CCH(NH_2)CH(CH_3)CH_2CH_3$. Isoleucine is an essential amino acid. FIG. 2 shows the chemical formula of Isoleucine.

Leucine is used as a source of energy. Leucine helps reduce muscle protein breakdown and promotes healing of skin. Leucine (abbreviated as Leu or L) is an $\alpha$-amino acid with the chemical formula $HO_2CCH(NH_2)CH_2CH(CH_3)_2$. Leucine is an essential amino acid, which means that humans cannot synthesize it. FIG. 3 shows the chemical formula of Leucine.

Lysine plays a major role in calcium absorption, building muscle protein, recovering from injuries, and the body's production of hormones, enzymes, and antibodies. It also is helpful in the formation of collagen. Lysine (abbreviated as Lys or K) is an $\alpha$-amino acid with the chemical formula $HO_2CCH(NH_2)(CH_2)_4NH_2$. Lysine is an essential amino acid. FIG. 4 shows the chemical formula for lysine.

Methionine reduces blood cholesterol levels, helps remove toxic wastes, and also may increase antioxidant levels. Methionine is abbreviated as Met or M. Methionine is an $\alpha$-amino acid with the chemical formula $HO_2CCH(NH_2)CH_2CH_2SCH_3$. Methionine is an essential amino acid. FIG. 5 shows the chemical formula for Methionine.

Proline is a major constituent of collagen and a major component in the formation of connective tissue (such as collagen) and heart muscle. Proline is readily mobilized for muscular energy. (Rosenbloom et al, "Incorporation of 3,4-Dehydroproline into Protocollagen and Collagen," *The Journal of Biological Chemistry*, vol. 245 pp 3361-3368. Uitto et al, "Incorporation of Proline Analogs into Procollagen", *Archives of Biochemistry and Biophysics* 181 (1977) pp. 293-299.) Proline is abbreviated as Pro or P and is an $\alpha$-amino acid. Proline is not an essential amino acid, which means that humans can synthesize it. FIG. 6 shows the chemical formula for proline.

Carnosine (beta-alanyl-L-histidine) is a dipeptide of the amino acids beta-alanine and histidine. Carnosine is a particularly effective anti-aging compound when injected. Carnosine has been proven to scavenge reactive oxygen species (ROS) as well as alpha-beta unsaturated aldehydes formed from peroxidation of cell membrane fatty acids during oxidative stress. Carnosine can oppose glycation and can chelate divalent metal ions. Chronic glycolysis is suspected to accelerate aging. A 2001 report published in *LeMagazine* noted, "Carnosine is the only agent that has shown multi-modal protective effects against protein degradation and cellular senescence"—otherwise known as aging. According to studies cited in the report, profound changes take place in the dermis, where collagen begins to break down. The Skin Stimulation Solution is injected directly into the dermis where the carnosine and other properties can begin to help restore elasticity and youthful tone to the skin." FIG. 7 shows the chemical formula for carnosine.

Dimethylaminoethanol, also known as DMAE or dimethylethanolamine, is an organic compound. This compound also goes by the names of N,N-dimethyl-2-aminoethanol, beta-dimethylaminoethyl alcohol, beta-hydroxyethyldimethylamine and Deanol. DMAE is a liquid with a color that ranges from clear to pale-yellow. DMAE adds the benefit that injecting the composition tightens skin as it rejuvenates. Most recently touted by board certified clinical and research dermatologist Dr. Nicholas Perricone, naturally occurring DMAE promotes anti-aging properties including improved appearance, elasticity and luminosity, while also enhancing the appearance of facial contours. FIG. 8 shows the chemical formula for DMAE.

Glucosamine ($C_6H_{13}NO_5$) is an amino sugar and a prominent precursor in the biochemical synthesis of glycosylated proteins and lipids. FIG. 9 shows the chemical formula for glucosamine. Glucosamine is commonly used as a treatment for osteoarthritis. However, the American Academy of Dermatology says that a recent study shows that glucosamine could prove to be an effective treatment to reverse the effects of skin cells damaged by UV exposure and to normalize pigment overproduction in skin cells. Glucosamine is a precursor for hyaluronic acid. In addition, a recent study supervised by Alexa Kimball, MD, assistant professor of dermatology at the Harvard Medical School, researched the effect of N-acetyl glucosamine and niacinamide (a B vitamin) in in vitro human skin cultures, as well as clinical trials on women aged 35-60 with moderate to fine wrinkles. The study found that the two complexes stimulated the production of hyaluronic acid, a key process in the rehydration of skin, as well as increased collagen expression.

Pyridoxine is one of the compounds that can be called vitamin B6, assists in the balancing of sodium and potassium as well as promoting red blood cell production. It has been suggested that Pyridoxine may also prevent eczema, and psoriasis. In addition, pyridoxine can help balance hormonal changes in women and aid in immune system. FIG. 10 shows the chemical formula of pyridoxine.

Other features that are considered as characteristic for the invention are set forth in the appended claims.

Although the invention is illustrated and described herein as embodied in an injectable amino-acid composition, it is nevertheless not intended to be limited to the details shown, since various modifications and structural changes may be made therein without departing from the spirit of the invention and within the scope and range of equivalents of the claims.

The composition and method of use of the invention, however, together with additional objects and advantages thereof will be best understood from the following description of specific embodiments when read in connection with the accompanying examples.

DETAILED DESCRIPTION OF THE INVENTION

Figure 1:
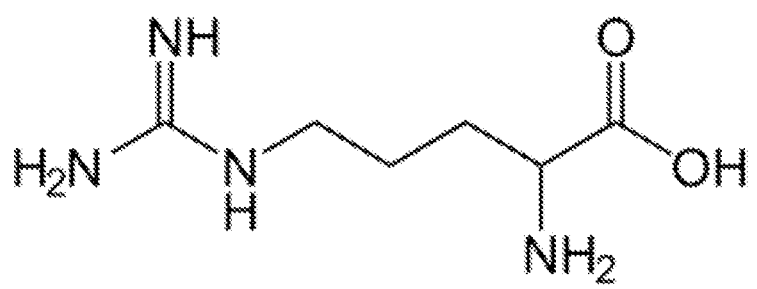
FIG. 1 shows the chemical formula of arginine.
Figure 2:
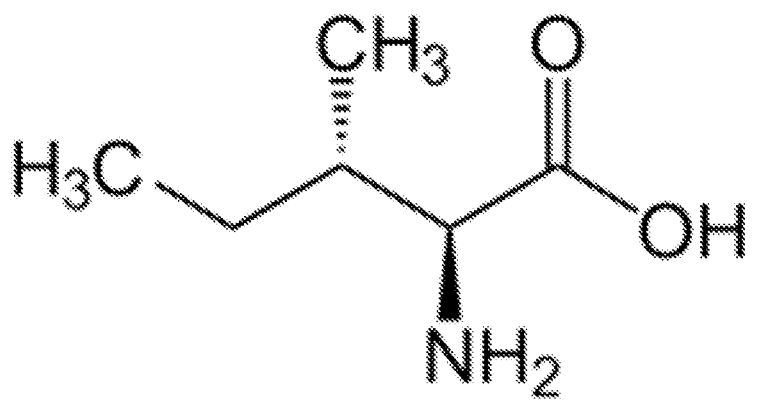
FIG. 2 shows the chemical formula of isoleucine.
Figure 3:
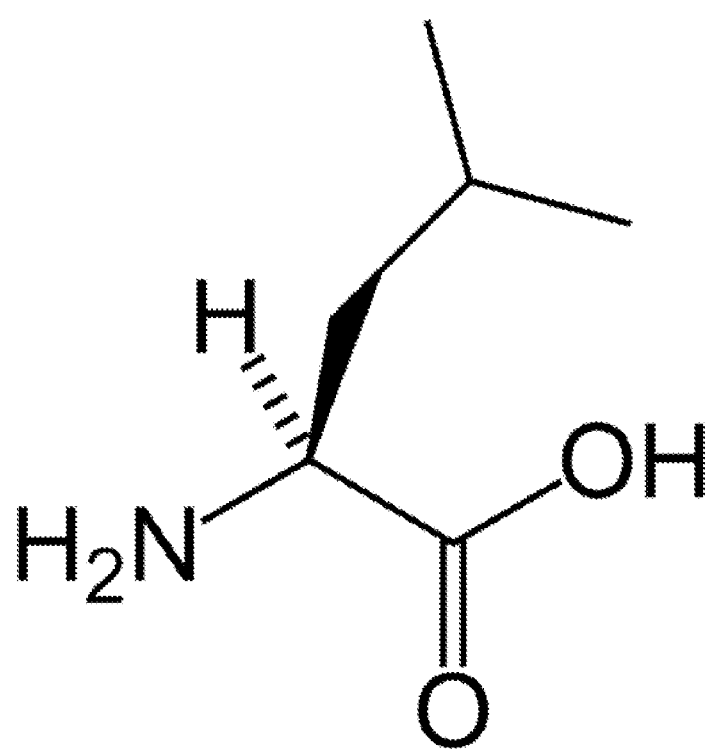
FIG. 3 shows the chemical formula of leucine.
Figure 4:
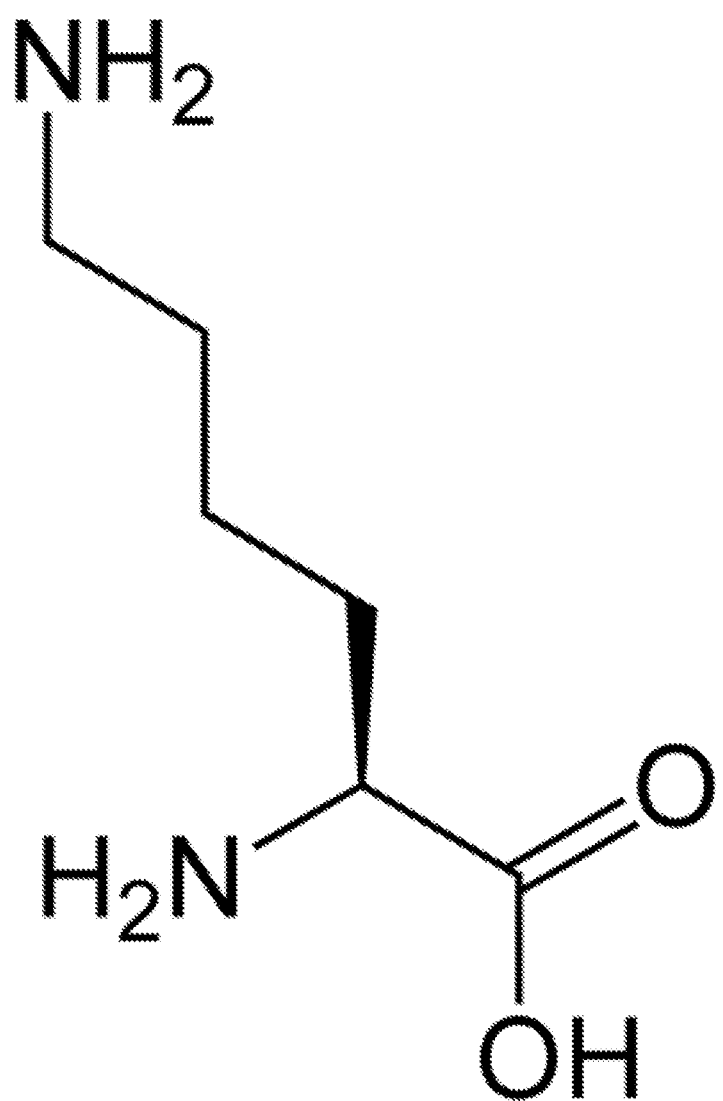
FIG. 4 shows the chemical formula of lysine.
Figure 5:
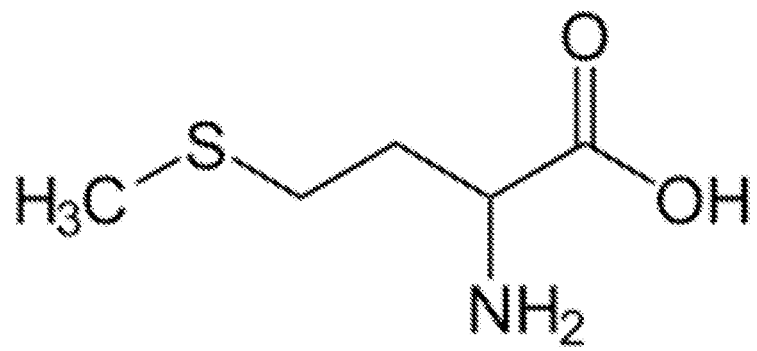
FIG. 5 shows the chemical formula of methionine.
Figure 6:
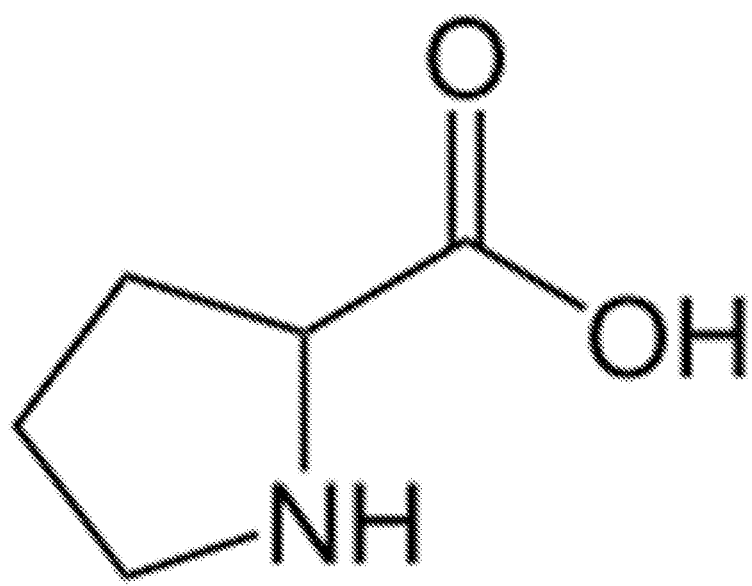
FIG. 6 shows the chemical formula of proline.
Figure 7:
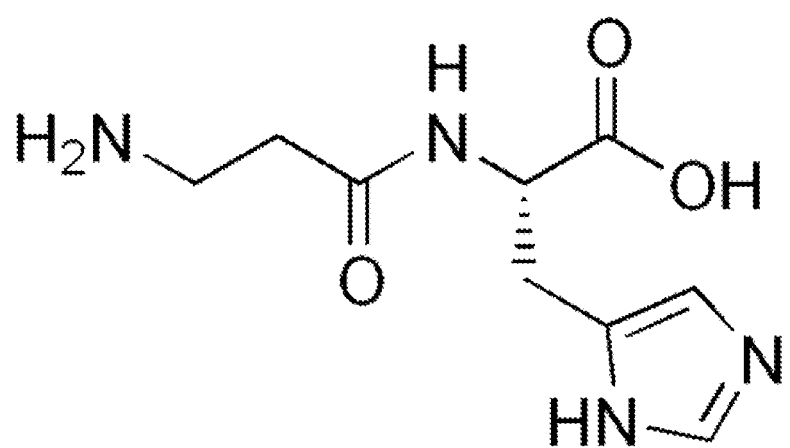
FIG. 7 shows the chemical formula of carnosine.
Figure 8:
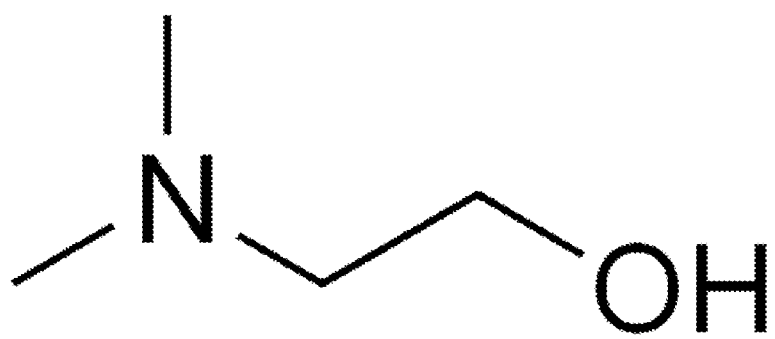
FIG. 8 shows the chemical formula of DMAE.
Figure 9:
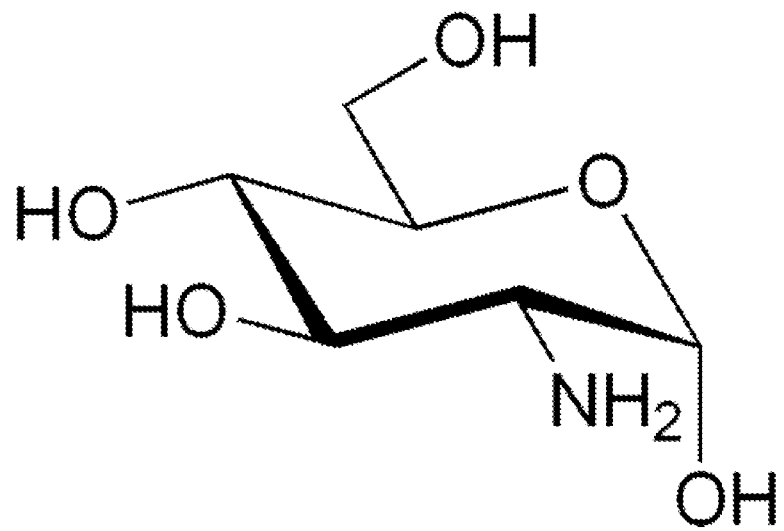
FIG. 9 shows the chemical formula of glucosamine.
Figure 10:
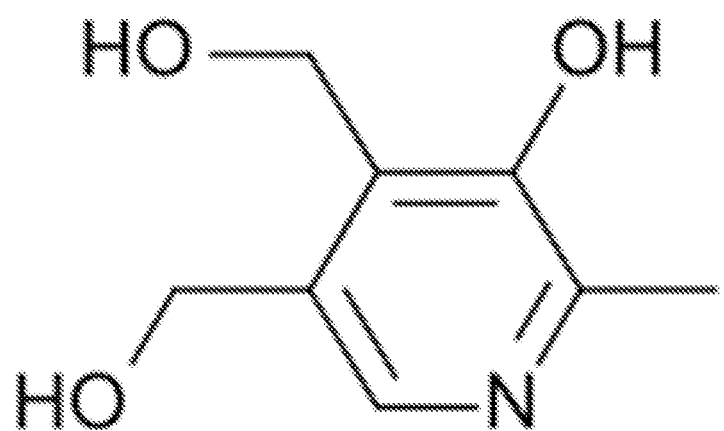
FIG. 10 shows the chemical formula of pyridoxine.

Referring now to the below-listed example, there is seen an injectable amino-acid composition. The composition includes the following ingredients.

| INGREDIENT | WEIGHT PERCENTAGE |
|---|---|
| Water | 98.98099 |
| Sodium Chloride | 0.89901 |
| DMEA | 0.01 |
| Glucosamine HCl | 0.05 |
| Pyridoxine HCl | 0.05 |
| Lysine HCl | 0.001429 |
| Arginine HCl | 0.001429 |
| Leucine | 0.001429 |
| Isoleucine | 0.001429 |
| Methionine | 0.001429 |
| Carnosine | 0.001429 |
| Proline | 0.001429 |

In a preferred embodiment, the composition has a pH as near 7 as possible. A preferred range of pH is 6.0 to 7.4. To create the neutral pH, preservatives such as sodium metabisulfite, which create a pH of 5, should be avoided. By maintaining a pH near 7, injected tissue maintains physiciolgial normothermia (i.e. 36.8 to 37.2° C.). Maintaining a normal pH in injected tissue preserves the intercellular matrix and thereby prevents tissue damage. As an additional result, the injections are less painful.

The composition is strategically injected into targeted areas of the dermis layer of the skin (4 mm deep). The solution may be injected either alone or prior to dermal filler injectables or botulinum-toxin. The dermis layer can be considered the mattress of the skin where collagen and elastin fibers form the coils.

Preferably, the composition is administered in four treatments, two weeks apart. Depending on skin damage, dehydration level, and repair needed, treatments can be increased as needed. A follow-up treatment is suggested every three to four months. This works as a complementary treatment prior to dermal fillers and botulinum-toxin injections.

The volume of the amino-acid solution to be injected in a given injection is 0.1 mL. A typical combined volume of injections at a given site is 0.5 mL. Injecting less than 0.1 mL will decrease the efficacy of the injection. Injecting more than 0.5 mL at a given site can damage the tissue.

In a preferred embodiment of the method, the solution is to be injected on the same day, but before injecting the skin with fillers or botulinum toxin.

The amino-acid composition is injected after injecting the site with fillers or botulinum toxin to help the skin heal. A typical injection time is one week after the injection of fillers or botulinum toxin.

I claim:

1. A method for promoting skin repair, which comprises delivering at least 0.1 mL of an amino-acid composition to a dermis of a patient at a given site during a given treatment, said amino-acid composition including proline, said proline having a weight percentage in said amino-acid composition of 0.0014.

2. The method according to claim 1, wherein said amino-acid composition includes an amino acid selected from the group consisting of lysine, arginine, leucine, isoleucine, and methionine.

3. The method according to claim 1, wherein said amino-acid composition includes at least one of glucosamine, pyridoxine, and carnosine.

4. The method according to claim 1, wherein the dermis receiving the amino-composition is an area to be treated.

5. The method according to claim 1, wherein said dermis is located in an anatomical location selected form the group consisting of a face, skin around eyes, cheeks, upper lip, oral commissures, jaw line, neck, décolleté, and cleavage.

6. The method according to claim 1, which further comprises injecting dermal tissue surrounding the dermis with botulinum toxin after delivering the amino-acid composition.

7. The method according to claim 1, which further comprises injecting dermal tissue surrounding the dermis with a dermal filler after delivering the amino-acid composition.

8. A method for promoting skin repair, which comprises injecting a volume no greater than 0.5 mL of an amino-acid composition into a dermis of a patient at a given site during a given treatment, the amino-acid composition including proline, said proline having a weight percentage in said amino-acid composition of 0.0014.

9. The method according to claim 1, wherein the delivering of the amino-acid composition is performed by injecting the dermis.

10. The method according to claim 1, which further comprises performing the delivering step on a same day but before injecting botulinum toxin or a filler.

11. The method according to claim 1, which further comprises performing the delivering step after injecting botulinum toxin or a filler.

12. The method according to claim 11, wherein the delivering step is performed at least seven days after injecting the botulinum toxin or the filler.

13. The method according to claim 1, wherein said amino-acid composition further includes Glucosamine HCl, Pyridoxine HCl, Lysine HCl, Arginine HCl, Leucine, Isoleucine, Methionine, and Carnosine.

14. The method according to claim 1, wherein said amino-acid composition has a pH between 6.0 and 7.4.

15. The method according to claim 8, which comprises injecting at least 0.1 mL of said amino-acid composition at the site.

16. A method for promoting skin repair, which comprises delivering an amino-acid composition to a dermis of a patient at a given site during a given treatment, said amino-acid composition including proline and having a pH between 6.0 and 7.4, said proline having a weight percentage in said amino-acid composition of 0.0014.

* * * * *